US012653791B2

(12) United States Patent (10) Patent No.: US 12,653,791 B2
Brams et al. (45) Date of Patent: Jun. 16, 2026

(54) TRIMODAL, PRECISION-TIMED PULSATILE RELEASE TABLET

(71) Applicant: Cingulate Therapeutics LLC, Morristown, NJ (US)

(72) Inventors: Matthew Brams, Houston, TX (US); Raul Silva, Upper Grandview, NY (US); Arthur Straughn, Cordova, TN (US)

(73) Assignee: Cingulate Therapeutics LLC, Morristown, NJ (US)

( * ) Notice: Subject to any disclaimer, the term of this patent is extended or adjusted under 35 U.S.C. 154(b) by 228 days.

(21) Appl. No.: 18/560,039

(22) PCT Filed: May 10, 2022

(86) PCT No.: PCT/US2022/028550
§ 371 (c)(1),
(2) Date: Nov. 9, 2023

(87) PCT Pub. No.: WO2022/240849
PCT Pub. Date: Nov. 17, 2022

(65) Prior Publication Data
US 2024/0238208 A1 Jul. 18, 2024

Related U.S. Application Data

(60) Provisional application No. 63/187,037, filed on May 11, 2021.

(51) Int. Cl.
| *A61K 9/20* | (2006.01) |
| *A61K 9/00* | (2006.01) |
| *A61K 9/24* | (2006.01) |
| *A61K 31/4458* | (2006.01) |

(52) U.S. Cl.
CPC ............ *A61K 9/209* (2013.01); *A61K 9/0053* (2013.01); *A61K 9/2009* (2013.01); *A61K 9/2013* (2013.01); *A61K 9/2054* (2013.01); *A61K 9/2059* (2013.01); *A61K 31/4458* (2013.01)

(58) Field of Classification Search
None
See application file for complete search history.

(56) References Cited

U.S. PATENT DOCUMENTS

| 9,833,412 | B2 | 12/2017 | Toneguzzo et al. |
| 10,561,618 | B2 | 2/2020 | Hansen et al. |
| 2003/0194439 | A1 | 10/2003 | Midha et al. |
| 2013/0022676 | A1* | 1/2013 | Mullen ................ A61K 31/437 |
| | | | 514/249 |
| 2016/0250148 | A1* | 9/2016 | Brams ..................... A61P 25/14 |
| | | | 424/465 |
| 2020/0146991 | A1 | 5/2020 | Brams et al. |

FOREIGN PATENT DOCUMENTS

| CN | 1977845 A | 6/2007 |
| EP | 0313535 B1 | 7/1994 |

OTHER PUBLICATIONS

Cingulate® Technology Cingulate's Precision Timed Release (PTR) Platform Technology.*
"International Search Report and Written Opinion Issued in PCT Application No. PCT/US2022/028550", Mailed Date: Aug. 11, 2022, 11 Pages.
Silva et al., (2018) "Pharmacoscintigraphic and Pharmacokinetic Analysis of CTx-1301, a Novel Tri-modal Oral Formulation for Release of Dexmethylphenidate in Healthy Adults", https://www.cingulate.com/static-files/049389ce-6e57-4017-a021-5ee3ca84239c#:~:text=Results%3A%20The%20two%20CTx%2D1301,XR%C2%AE%20(3.0%20hours), 1 page.
Extended European Search Report dated Jan. 23, 2026 in PCT/US2023013139 (8 pages).

* cited by examiner

*Primary Examiner* — Susan T Tran
(74) *Attorney, Agent, or Firm* — Mintz, Levin, Cohn, Ferris, Glovsky and Popeo, P.C.

(57) ABSTRACT

A trimodal, precision-timed pulsatile release tablet that delivers a trimodal (i.e., three pulses) release profile is provided. The tablet includes at least three stimulant layers. By providing a single tablet with multiple stimulant layers, the dosing frequency is decreased, and compliance is expected to increase since precise blood levels of the active pharmaceutical ingredient over a prolonged time period are controlled and achieved.

19 Claims, 4 Drawing Sheets

100

Ø11.00
[.4331]

0.51
[.0200]

1.58 CUP DEPTH
[.0620]

102

R3.81
[.1500]

103

101

Ø11.00
[.4331]

R38.81
[1.5280]

BLENDED LAND 3.15
[.1240]

0.51
[.0200]

6.30
[.2480]

100

IMMEDIATE RELEASE (d-MPH)
104

ORALOGIK™
EROSION BARRIERS
120

DELAYED, SUSTAINED RELEASE (d-MPH)
106

DELAYED, IMMEDIATE RELEASE (D-MPH)
108

122

106

108

104

PLASMA DEXMETHYLPHENIDATE (dMPH) CONCENTRATION VS TIME

LOW DOSE

PLASMA DEXMETHYLPHENIDATE (dMPH) CONCENTRATION VS TIME

HIGH DOSE

TRIMODAL, PRECISION-TIMED PULSATILE RELEASE TABLET

CROSS-REFERENCE TO RELATED APPLICATIONS

This application is a U.S. National Phase Application under 35 U.S.C. § 371 of International Patent Application PCT/US2022/028550, filed May 10, 2022, which claims the benefit of priority to U.S. Provisional Application No. 63/187,037, filed May 11, 2021 which is hereby incorporated by reference in its entirety.

BACKGROUND OF THE INVENTION

Since the introduction of modified-release stimulant dosage forms for the treatment of conditions such Attention Deficit Hyperactivity Disorder (ADHD), the need for administering an immediate release dosage form two to three times per day has been reduced to a single daily dose. For example, patients may respond to a single daily tablet or capsule that releases the stimulant as two distinct pulses—the first pulse occurring at the time of dosing and a second pulse 3 to 5 hours later. Such modified dosage forms typically provide therapeutically effective coverage for 8 to 12 hours after administration to a patient. However, many patients still require a separate, additional "booster" dose in the afternoon to maintain adequate therapeutic coverage throughout the entire day. Furthermore, as the level of stimulant concentration in blood decreases during the latter portions of the day, patients may experience a crash or rebound effect than can result in worsening of clinical symptoms or other effects, such as irritability.

There remains a need for a single, once-daily oral dosage form that delivers a stimulant drug in a manner that provides a safe and effective therapeutic response over the patient's active day.

SUMMARY OF THE INVENTION

A trimodal, precision-timed pulsatile release tablet that delivers a three-pulse release profile is provided. According to one embodiment, the tablet includes three stimulant layers inside the final tablet. By providing a single tablet having multiple stimulant layers, the dosing frequency is decreased, compliance is increased, and precise blood levels of the active pharmaceutical ingredient (API; e.g., the stimulant) are achieved over a prolonged time period.

The trimodal, precision-timed pulsatile release tablets disclosed herein provide a pharmaceutically precise amount of stimulant initially to the patient to cause the desired pharmacological response via a first stimulant layer and deliver the remaining predetermined amounts of stimulant via second and third stimulant layers to maintain the effective therapeutic pharmacological activity for a period of time in excess of the time expected from a single, bimodal drug formulation (immediate release followed by a second, delayed release).

According to one embodiment, the tablet includes a first stimulant layer having a first pulse of stimulant of about 25% to about 45% of the total stimulant in the tablet; a second stimulant layer having a second pulse of stimulant of about 35% to about 55% of the total stimulant in the tablet; and a third stimulant layer having a third pulse of stimulant of about 10% to about 30% of the total stimulant in the tablet, so that the total dose or label claim of the stimulant in the final tablet is 100%.

According to one embodiment, the tablet is structured such that the first stimulant layer is positioned on the exterior of the tablet and on an outer erosion barrier layer; the second stimulant layer is positioned between the outer erosion barrier layer and an inner erosion barrier layer such that it is surrounded by the outer and inner erosion barrier layers; and the third stimulant layer is positioned at the center of the tablet and surrounded by the inner erosion barrier layer.

By positioning the first stimulant layer on the exterior of the tablet, the first stimulant pulse can be released within about 10 minutes to about 45 minutes after administration to a patient. By surrounding the second and third stimulant layers with erosion barrier layers, the second and third stimulant pulses can be delayed releases. The delivery of the second stimulant pulse can be delayed until about 3 to about 5 hours following administration of the tablet to a patient. The delivery of the third stimulant pulse can be delayed until about 6 to about 10 hours following oral administration of the tablet to a patient.

The outer and inner erosion barrier layers each comprise about 30% to about 50% by weight of glyceryl behenate, about 40% to about 60% by weight of two or more grades of low-substituted hydroxypropyl cellulose (L-HPC), and about 4% to about 8% by weight of hydroxypropyl cellulose. The two or more grades of L-HPC can be LH-21 and LH-32.

The tablets described herein are to be administered orally in a pharmaceutically effective amount to a patient once daily to treat or prevent a variety of disorders, conditions, and diseases. According to one embodiment, administration of at least one stimulant may be carried out in order to treat any disorder, condition, or disease for which a stimulant is generally indicated in the present or the future. Such disorders, conditions, and diseases include, for example, ADHD, narcolepsy, acute depression, obesity and other eating disorders, including binge eating disorder. Stimulants may also be used in the treatment of individuals suffering from cognitive decline associated with AIDS, or AIDS-related conditions, or traumatic brain injury (TBI), mood elevation in terminally ill patients suffering from a disease such as cancer, chronic fatigue, menopausal executive function, sluggish cognitive tempo (SCT), autistic spectrum disorder, depression, conduct disorders, impulse control disorders, chemotherapy-induced lethargy, and fibromyalgia.

The tablets described herein can be effective in methods for extending the therapeutic duration of a stimulant. In such methods, the therapeutic duration of the stimulant may be effective for greater than 12 hours and up to 16 hours after oral administration of the tablet to a patient.

Suitable stimulants delivered according to the provided tablet include any of a variety of stimulants suitable for treatment of the disorders provided. Particularly suitable stimulants include methylphenidate-based agents.

DETAILED DESCRIPTION OF THE INVENTION

As used in the specification and the appended claims, the singular forms "a," "an," and "the" include plural referents unless the context clearly dictates otherwise.

"Active ingredient" and "pharmacologically active ingredient" are used herein to refer to a chemical material or compound which induces a desired pharmacologic effect.

"Stimulant" as used herein refers to any active pharmaceutical ingredient administered to induce temporary improvements in either mental or physical functions or both.

"Methylphenidate" as used herein, includes all four optical isomers of the compound (d-threo-methylphenidate, 1-threo-methylphenidate, d-erythro-methylphenidate, and 1-erythro-methylphenidate) and all pharmaceutically acceptable salts, metabolites and prodrugs thereof, including a racemic mixture of d-threo methylphenidate and 1-threo methylphenidate as well as methylphenidate hydrochloride.

"Pulsed-release," "pulsed-release drug delivery system," "pulsatile release," "pulsatile precision-timed release" or "pulsatile drug delivery system" refers to a single tablet that aims to release one or more active ingredients in multiple pulses in a programmed pattern, i.e., at appropriate, predetermined times that are separated by active ingredient release-free intervals or lag-time, and in appropriate, predetermined amounts.

"Effective amount" or "pharmaceutically effective amount" of an agent as provided herein is meant to refer to a sufficient amount of an active ingredient to provide the desired therapeutic effect.

It is to be noted that terms such as "first", "second", "third", "top", "bottom", "upper", "lower" are applied foremostly for purposes of clarity and distinguishing one element or object from another. Such terms, especially "top", "bottom", "upper", and "lower" are relative and dependent of the orientation of an object (e.g., tablet) which may be same as or different from the orientations of the same object presented in the figures provided herein.

Figure 1A:
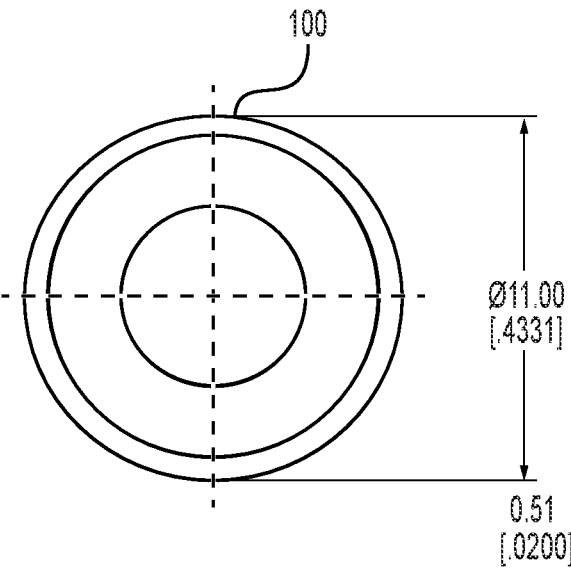
FIG. 1A is a top view of one embodiment of a trimodal, pulsatile release tablet disclosed herein.
Figure 1B:
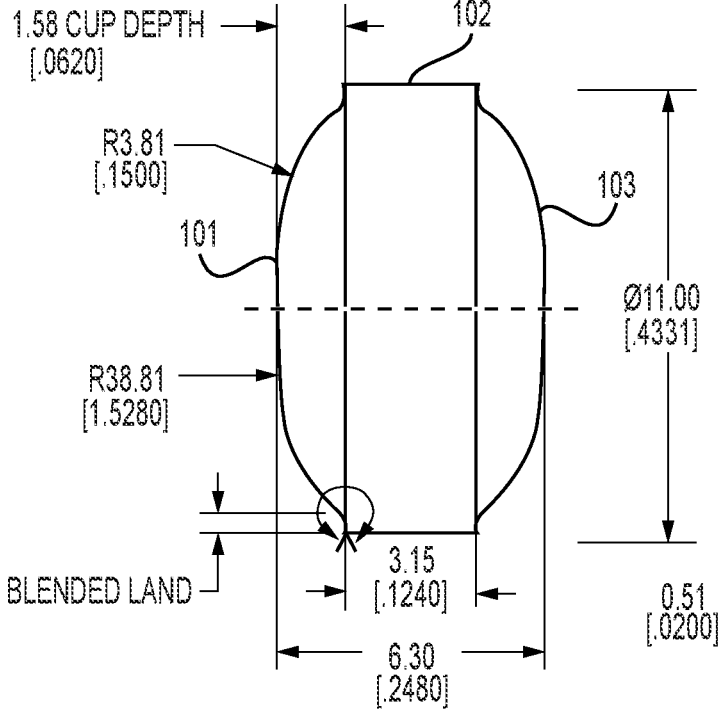
FIG. 1B is a perspective view of one embodiment of a trimodal, pulsatile release tablet disclosed herein.

FIGS. 1A and 1B provide a top view and perspective view, respectively, of an embodiment of a tablet 100. FIG. 1A shows a round biconvex tablet. As shown in FIG. 1B, the tablet (100) includes a cylindrical central band section (102) or "belly bend" around the center of the tablet (100). The top (101) and bottom (103), oriented as left and right, respectively in FIG. 1B of the tablet (100) are shown as multiple radii convex sections, which provide the tablet (100) with a symmetrical appearance. As each convex section has the same features, any references to the structure of one convex section may be considered a reference to the other convex section, unless indicated otherwise. Each end of the convex section curves away from the band section (102) to a flat surface of the convex section. As shown in FIG. 1B, the portions of the first stimulant layer (104) identified as "blended land" are the flat section between the cup and the belly band. The size of the blended land helps with the structural integrity of the tablet. Without an appropriately sized "land" the compression forces across the erosion barrier layers would not be uniform and the relaxation force after compression could cause delamination/splitting and impact the release timing.

The diameter of the tablet (100) can be from about 9.00 mm to about 13.00 mm, or from about 10.00 mm to about 12.00 mm. In one embodiment, as shown in FIGS. 1A and 1B, the diameter is 11.00 mm.

The distance between the center of each convex section (i.e., the peak points A and B on the top (101) and bottom (103) of the tablet), which define the overall thickness of the tablet (100), is from about 5.00 mm to about 8.00 mm, or from about 6.00 mm to about 7.00 mm. In one embodiment, as shown in FIG. 1B, the distance between the peak points A and B is about 6.30 mm. The width of central band (102) can be from about 40% to about 60% of the distance between the peak points A and B, or from about 45% to about 55%, or about 50%. In one embodiment, as shown in FIG. 1B, the width of central band (102) is 50% of the distance between the peak points A and B, or 3.15 mm.

Figure 2:
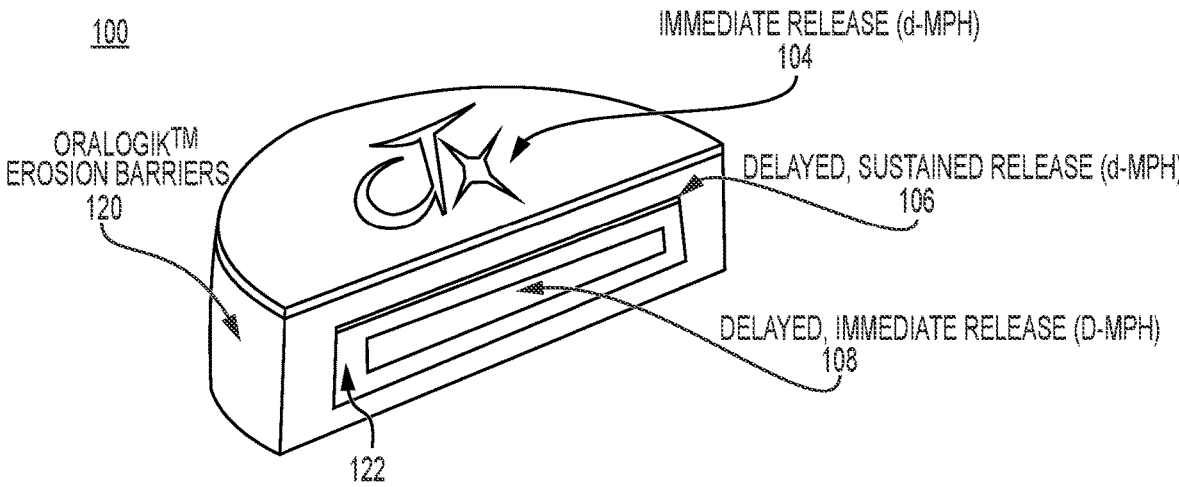
FIG. 2 is a cross-sectional diagram of one embodiment of a trimodal, pulsatile release tablet disclosed herein.

As illustrated in FIG. 2, the tablet (100) can include three stimulant layers (104), (106), and (108), respectively, separated by erosion barrier layers (outer erosion barrier layer (120) and inner erosion barrier layer (122)). The three stimulant layers are located separate and apart from each other in the tablet (100); e.g., at specific and controlled positions within the tablet. As shown in FIG. 2, the first stimulant layer (104), containing a first stimulant pulse is positioned on the exterior, or on the top (101), of the tablet (100). Immediately beneath the first stimulant layer (104), unit is an outer erosion barrier layer (120). A second stimulant layer (106), containing a second stimulant pulse, is positioned between the outer erosion barrier layer (120) and an inner erosion barrier layer (122), such that the second stimulant layer (106) is completely surrounded by the outer and inner erosion barrier layers. A third stimulant layer (108), containing a third stimulant pulse is positioned at the center or core of the tablet. The inner erosion barrier layer (122) completely surrounds a third stimulant layer (108). As shown in FIG. 2, the second stimulant layer is positioned between the first and third stimulant layers. An alternative arrangement is show in FIG. 3 where the first stimulant layer is provided on the bottom of the outer erosion barrier layer, such that the third stimulant layer is positioned between the first stimulant layer and the second stimulant layer.

The first stimulant layer (104), is designed for release of a first stimulant pulse immediately following oral administration of the tablet (100) to a patient (i.e., immediate release or IR). The IR can be substantially complete within about 10 minutes to about 45 minutes after oral administration of the tablet to a patient or about 20 minutes to about 30 minutes after oral administration of the tablet to a patient. In one embodiment, the IR is substantially complete within 30 minutes after oral administration of the tablet to a patient. In this context, "substantially complete" can mean release of no less than 90% of the first pulse.

The second and third stimulant layers (106) and (108) are designed for delayed release of the second and third stimulant pulses, respectively. The delayed releases are achieved by the erosion barrier layers and positioning of the second and third stimulant layers within the tablet.

Since the first stimulant layer (104) is designed for immediate release of the first stimulant pulse, the first stimulant layer (104) is located on the exterior of the tablet (100), e.g., top (101). As a result, the first stimulant layer (104) is readily available for dissolution immediately after administration to a patient thereby releasing the first stimulant pulse. The bottom surface of the first stimulant layer is bordered by the outer erosion barrier layer (120).

The first stimulant layer is approximately 549-600 microns thick and covers the entire top surface of the tablet (100) following the contour of the outer tablet surface (101).

According to one embodiment, the first stimulant layer (104) releases from about 25% to about 45% of the total stimulant in the tablet, or from about 30% to about 40%, or about 35%.

The second stimulant layer (106) is designed for release of a second stimulant pulse that begins about 2 hours to about 5 hours following administration of the tablet to a patient (i.e. delayed release or DR). According to another embodiment, release of the second stimulant pulse begins about 3 to about 5 hours following administration of the tablet to a patient. According to one embodiment, release of the second stimulant pulse begins about 3 to about 4 hours following administration of the tablet to a patient. According to one embodiment, release of the second stimulant pulse begins about 3 hours following administration of the tablet to a patient. According to another embodiment, release of the second stimulant pulse begins about 3.5 hours following administration of the tablet to a patient. The second stimulant layer may be approximately 549-750 microns thick.

According to certain embodiments, the second pulse is from about 35% to about 55% of the total stimulant in the tablet, or from about 40% to about 50%, or from about 45% to about 50%. In one embodiment, the second pulse is about 45% of the total stimulant in the tablet.

The second pulse is released over a time period (i.e., sustained release or SR). According to one embodiment, the second pulse release is sustained for about 30 minutes to about 135 minutes. According to another embodiment, release of the second pulse is sustained about 45 minutes to about 120 minutes. According to another embodiment, release of the second pulse is sustained for about 60 minutes to about 100 minutes. According to another embodiment, the second pulse is released over a time period of about 100 minutes. According to another embodiment, release of the second pulse is sustained for about 90 minutes.

The third stimulant layer (108) is a delayed, immediate release, containing the third stimulant pulse can be positioned at the center of the tablet. The third stimulant release layer is approximately 1.97-2.03 mm thick×4.95-5.05 mm in diameter with a flat-faced radius edge.

According to one embodiment, the third stimulant layer (108) includes a third pulse that is delayed in release until about 5 hours to about 10 hours following oral administration of the tablet to a patient. According to another embodiment, release of the third pulse begins about 6 hours to about 9 hours following oral administration of the tablet to a patient. According to another embodiment, release of the third pulse begins about 7 hours to about 8 hours following oral administration of the tablet to a patient. According to another embodiment, release of the third stimulant pulse is delayed until about 8 hours following oral administration of the tablet to a patient. According to another embodiment, release of the third pulse begins about 9 hours following oral administration of the tablet to a patient. The third stimulant pulse can be a delayed, immediate release pulse.

According to one embodiment, the third pulse is about 5% to about 20% of the total API in the tablet (100), or from about 10% to about 20%, or from about 15% to about 20%. According to another embodiment, the third pulse can be about 20% of the total stimulant in the tablet.

The outer and inner erosion barrier layers (120) and (122), collectively referred to as the "erosion barrier layers", can have the same composition. Although the outer erosion barrier layer (120) and the inner erosion barrier layer (122) are shown as separate structures in FIG. 2, in embodiments where the erosion barrier layers have the same composition, there may not be a clear physical boundary or distinction between the erosion barrier layers in the finished tablet.

The outer and inner erosion barrier layers can each comprise glyceryl behenate, a blend of low-substituted hydroxypropyl cellulose (L-HPC) and hydroxypropyl cellulose. L-HPCs are insoluble in water and comprise a glucose backbone that is substituted to a minimal extent by hydroxypropyl groups. This chemistry prevents dissolution of the L-HPCs but they swell in the presence of water. In certain embodiments, the erosion barrier layers can comprise two or more grades of L-HPCs, such as LH-21 and LH-32. LH-21 is moderately fibrous and has a mean particle size of 45 µm. LH-21 has a molecular weight of around 120,000 and a hydroxypropyl content of around 11%. LH-32 is micronized, with a mean particle diameter of 20 µm. LH-32 has a molecular weight of 115,000 and a hydroxypropyl cellulose content of 8%.

In one embodiment, the outer and inner erosion barrier layers each comprise about 30% to about 50% by weight of glyceryl behenate, 35% to about 45% of glyceryl behenate or about 37.5% to about 42.5% of glyceryl behenate. In one embodiment, the glyceryl behenate can be Compritol ATO 888.

The outer and inner erosion barrier layers can each comprise about 40% to about 60% total by weight of two or more grades of L-HPC, or about 45% to about 55% or about 47.5% to about 52.5%. In one embodiment, the outer and inner erosion barrier layers each comprise about 15% to about 25% by weight of a first grade of L-HPC, such as LH-21, and about 25% to about 35% by weight of a second grade of L-HPC, such as LH-32; about 20% to about 23% by weight of LH-21 and about 27.5% to about 32.5% by weight of LH-32.

The outer and inner erosion barrier layers can each comprise about 4% to about 8% by weight of hydroxypropyl cellulose. In certain embodiments, the outer and inner erosion barrier layers can each comprise about 5% to about 7% by weight of hydroxypropyl cellulose. In certain embodiments, the hydroxypropyl cellulose of the outer and inner erosion barrier layers can be hydroxypropyl cellulose Type L.

The erosion barrier layers may further include silicon dioxide, for example, colloidal silicon dioxide such as Aerosil 200 Pharma. In certain embodiments, the outer and inner erosion barrier layers each comprise about 1% or less by weight of colloidal silicon dioxide, about 0.2%-0.8% by weight of colloidal silicon dioxide or about 0.2% to 0.6% by weight of colloidal silicon dioxide.

Figure 4:
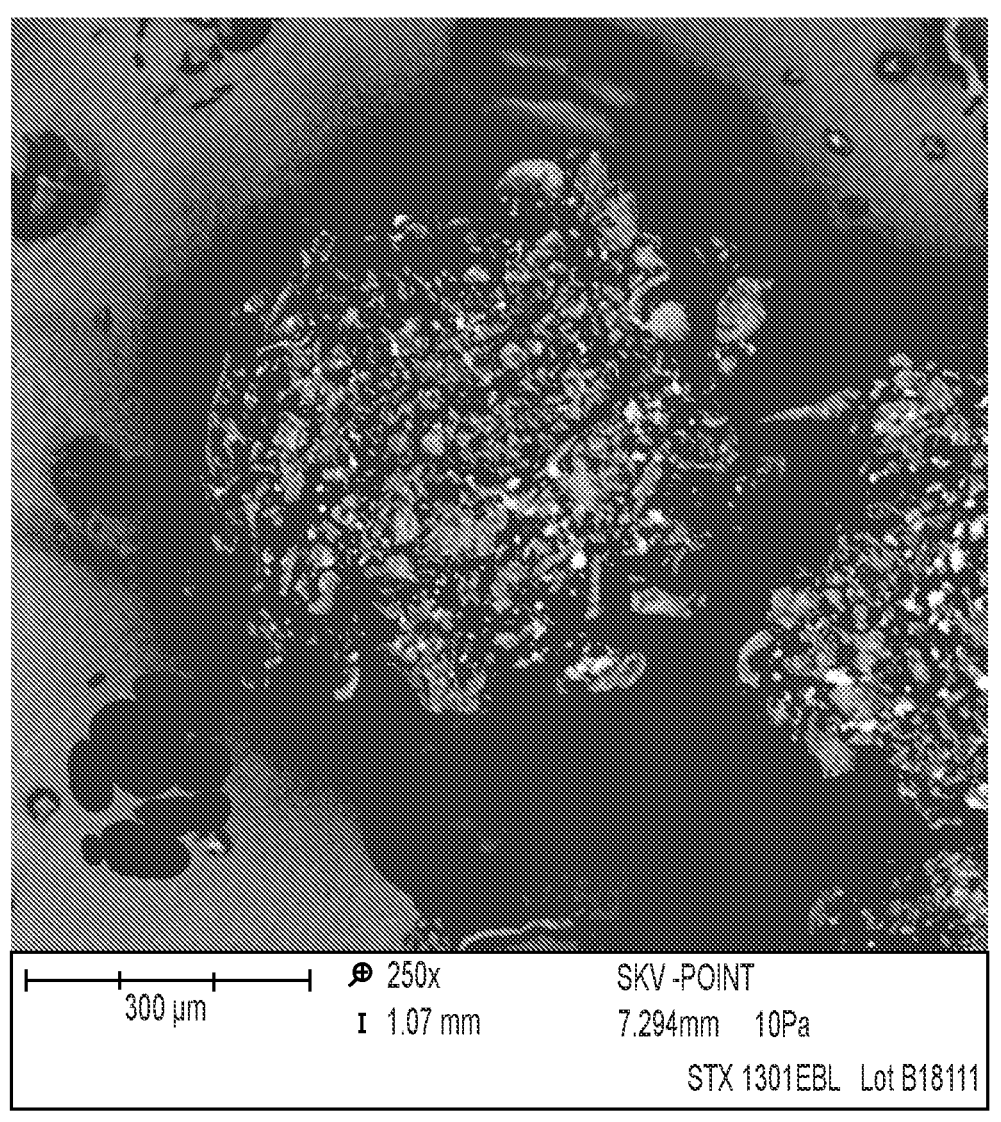
FIG. 4 shows a Scanning Electron Microscopy view of the granules making up the erosion barrier layers.

The pulsatile release profile of the tablets described, result, in part, from the composition of the outer and inner erosion barrier layers. FIG. 4 shows granules of the outer and inner erosion barrier layers with scanning electron microscopy. FIG. 4 shows the shape of the granules. The shape of the granules can help reduce the ingress of water by reducing the amount of void spaces between the granules and to ensure that the water absorbing or swelling components of the outer and inner erosion barrier layers are coated with hydrophobic, poorly soluble components. This helps ensure that the outer and inner erosion barrier layers are eroded/shed at a controlled rate so that the second and third pulses are exposed to the aqueous media and begin releasing at the desired times after oral administration of the tablet to a patient.

In certain embodiments, the trimodal, precision-timed pulsatile release tablet includes about 200-300 mg of the outer erosion barrier layer, about 225-275 mg, about 230-260 mg, or about 235-245 mg. In certain embodiments, the pulsed release tablet includes about 100-150 mg of the inner erosion barrier layer, about 115-135 mg or about 120-130 mg.

In certain embodiments, the thickness of the outer erosion barrier layer is about 574-888 microns.

In certain embodiments, the thickness of the inner erosion barrier layer is about 862-1071 microns.

The distance between the first and third stimulant layers (104, 108) is about 1,436-1,906 microns. As shown in FIG. 2, the distance between the first and third stimulant layers (104, 108) is about 1,567-1,932 microns.

Figure 3:
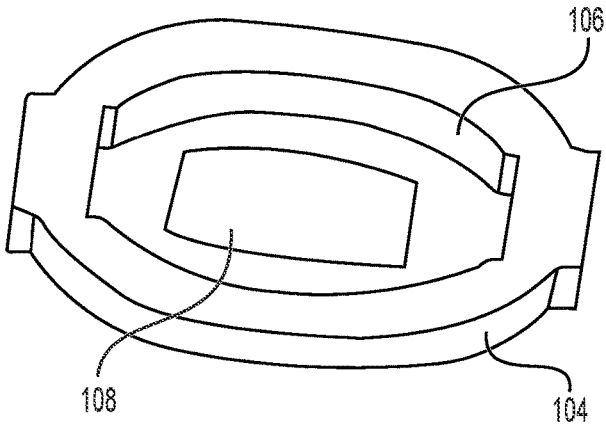
FIG. 3 is a computed tomography scan of another embodiment of a trimodal, pulsatile release tablet disclosed herein.

Similarly, the distance between the second and third stimulant layers (106, 108) is about 862-1071 microns. As shown in FIG. 2 and FIG. 3, the distance between the second and third stimulant layers (106, 108) is about 862-1071 microns.

In certain embodiments, each stimulant layer contains, in addition to the stimulant material, an excipient and a diluent. The amount of excipient and diluent in each stimulant layer depends on the total amount of stimulant in the tablet. Exemplary excipients include hypromellose (hydroxypropyl methylcellulose or HPMC), microcrystalline cellulose, colloidal silicon dioxide, sodium starch glycolate and sodium stearyl fumarate. In one embodiment, microcrystalline cellulose, colloidal silicon dioxide, sodium starch glycolate and sodium stearyl fumarate can be provided as a single composite excipient, such as Prosolv® EASYtab SP (JRS Pharma Rosenberg, Germany). In one embodiment, an additional diluent is calcium sulfate.

In certain embodiments, the first stimulant layer can contain from about 2.5 w/w % to about 25 w/w % of stimulant (active ingredient, e.g., methylphenidate). In one embodiment, the first stimulant layer can contain about 75 w/w % to about 98 w/w % of excipient including microcrystalline cellulose, colloidal silicon dioxide, sodium starch glycolate and sodium stearyl fumarate (such as Prosolv® EASYtab SP). In another embodiment, the first stimulant layer can contain about 3 w/w % or less of diluent (such as calcium sulfate). The amount of diluent can be 1 w/w %, which can be calcium sulfate.

In certain embodiments, the second stimulant layer can contain about 5 w/w % to about 50 w/w % of stimulant (active ingredient, e.g., methylphenidate). In one embodiment, the second stimulant layer can contain about 40 w/w % to about 90 w/w % total of microcrystalline cellulose, colloidal silicon dioxide, sodium starch glycolate and sodium stearyl fumarate (such as Prosolv® EASYtab SP) and about 4 w/w % to about 10 w/w % hypromellose. In another embodiment, the second stimulant layer can contain about 3 w/w % or less of diluent (such as calcium sulfate). The amount of diluent can be 1 w/w %, which can be calcium sulfate.

In certain embodiments, the third stimulant layer can contain about 2.5 w/w % to about 25 w/w % of stimulant (active ingredient, e.g., methylphenidate) (or doubled for racemic methylphenidate). In one embodiment, the third stimulant layer can contain about 75 w/w % to about 98 w/w % total of microcrystalline cellulose, colloidal silicon dioxide, sodium starch glycolate and sodium stearyl fumarate (such as Prosolv® EASYtab SP). In another embodiment, the third stimulant layer can contain about 3 w/w % or less of diluent (such as calcium sulfate). The amount of diluent can be 1 w/w %, which can be calcium sulfate.

Additionally, the lower proportional dose of the third release of the tablet creates a controlled decline of the stimulant concentration in plasma. The controlled decline is advantageous in that it can reduce or minimize the crash or rebound symptoms that are commonly associated with the dual-release Focalin® XR, Concerta® and Adderall XR®. Patients who take such dual-release medications frequently complain about unpleasant crash symptoms at around 5 to 7 hours after taking the medication. The common symptoms include nausea, digestive discomfort, depressive feelings, lack of energy or fatigue, irritability, increased anxiety, etc. In addition, common rebound symptoms mimic baseline core ADHD symptoms, but of greater intensity. This would include reduced ability to concentrate, worsening hyperactivity and impulsivity. Such drug wear-off episodes can be dangerous and present medical emergencies.

The tablets disclosed herein are suitable for the delivery of an effective amount of at least one stimulant and salts thereof. At least one other active ingredient may be combined with the stimulant in a single stimulant layer within the tablet, or one or more stimulant layers within the tablet may comprise the additional active ingredient. Salts of the active ingredients used in conjunction with the present tablets may be obtained commercially or can be prepared using standard procedures known to those skilled in the art of synthetic organic chemistry. Suitable stimulants include, but are not limited to, methylphenidate. The stimulants provided herein may be in the form of a pharmaceutically acceptable salt, prodrug, or other derivative or active metabolite. According to a particular embodiment, the stimulant is dexmethylphenidate or a pharmaceutically acceptable salt thereof. According to another embodiment, the stimulant is dexmethylphenidate hydrochloride (e.g., the d-threo-enantiomer of racemic methylphenidate hydrochloride).

Optional components present in the trimodal, precision-timed pulsatile release tablet can include, but are not limited to, additional binders, lubricants, disintegrants, stabilizers, surfactants, coloring agents, coatings, and diluents. Suitable diluents include, but are not limited to, dicalcium phosphate dihydrate, lactose, cellulose, kaolin, mannitol, sodium chloride, dry starch, hydrolyzed starches, silicon dioxide, titanium oxide, alumina, talc, microcrystal-line cellulose, and powdered sugar. Suitable binder materials include, but are not limited to, starch (including corn starch and pregelatinized starch), gelatin, sugars (including sucrose, glucose, dextrose, lactose and sorbitol), polyethylene glycol, waxes, natural and synthetic gums (e.g., acacia, tragacanth, sodium alginate, polyvinylpyrrolidone, celluloses, and Veegum), and synthetic polymers such as polymethacrylates and poly-vinylpyrroli-done. Suitable lubricants include, but are not limited to, magnesium stearate, calcium stearate, stearic acid, and polyethylene glycol. Suitable disintegrants include, but are not limited to, starches, clays, celluloses, algins, gums, or crosslinked polymers. Suitable surfactants include, but are not limited to, those containing carboxylate, sulfonate and sulfate ions, associated with cations such as sodium, potassium and ammonium ions; long alkyl chain sulfonates and alkyl aryl sulfonates such as sodium dodecyl-benzene sulfonate; dialkyl sodium sulfosuccinates, such as sodium bis-(2-ethylhexyl)-sulfosuccinate; and alkyl sulfates such as sodium lauryl sulfate. Nontoxic auxiliary substances such as wetting or emulsifying agents, pH buffering agents, and preservatives may also be included in the tablet or in the individual drug-containing stimulant layers.

In one embodiment, the trimodal, pulsatile release tablet is a film-coated tablet. Suitable film coatings include aqueous film coatings, such as Opadry® II (Colorcon, Inc., Harleysville, PA).

The trimodal, precision-timed pulsatile release tablet described herein can be useful in a method of treatment of a disorder, condition or disease for which a stimulant is generally indicated by administering the trimodal, pulsatile release tablet to a patient in need thereof. In one embodiment, the disorder, condition or disease is ADHD.

The trimodal, precision-timed pulsatile release tablet described herein can be useful in methods for extending the therapeutic duration of a stimulant by administering the tablet to a patient in need thereof. As a result of the proportioned tripulse release of stimulant, the therapeutic duration of the stimulant is effective for longer than 12 hours, at least 14 hours, and up to 16 hours, after oral administration of the tablet to a patient.

The trimodal, pulsatile release tablets disclosed herein are useful for reducing treatment emergent adverse events (TE-AEs). The trimodal, pulsatile release tablets may reduce the number of TEAEs and types of TEAEs compared to current treatments, such as Focalin XR, including TEAEs such as palpitations, tachycardia and euphoric mood.

The trimodal, pulsatile release tablets described herein can be manufactured through a series of tablet-within-a-tablet compression operations. For example, the third stimulant layer is compressed and then surrounded by or covered with the inner erosion barrier layer. The second stimulant layer is then compressed on top of the inner erosion barrier layer and then surrounded by or covered with the outer erosion barrier layer. The first stimulant layer is then compressed on top of the outer erosion barrier layer, such that the second stimulant layer is positioned between the first stimulant layer and the third stimulant layer. In another embodiment, the second stimulant layer is compressed on the bottom of the inner erosion barrier layer, such that the third stimulant layer is positioned between the first stimulant layer and the second stimulant layer.

As a further example of the manufacturing of the tablet, the inner erosion barrier layer material is compressed into the punch. The previously compressed core of the third stimulant layer is then placed on the surface of the inner erosion barrier layer fill material and compressed. The remainder of the inner EBL material is then put on top followed by the second stimulant layer.

The lower punch is again filled by the outer erosion barrier layer material. The previously compressed entity is enrobed by the outer erosion barrier layer and the first stimulant layer is compressed on top.

The tablet is then complete and ready for coating.

Example 1

The bioavailability of the trimodal, precision-timed pulsatile release tablet described herein is compared to Focalin XR. Focalin XR (dexmethylphenidate hydrochloride) extended-release capsules are an extended-release formulation of dexmethylphenidate with a bi-modal release profile. Each bead-filled Focalin XR capsule contains half the dose as immediate-release beads and half as enteric-coated, delayed-release beads, thus providing an immediate release of dexmethylphenidate and a second delayed release of dexmethylphenidate.

A trimodal, precision-timed pulsatile release tablet, such as those illustrated in FIGS. 1A, 1B and 2, may be manufactured with the apparatus and steps as provided herein. The pulsed release tablet may include a total of 6.25 mg of dexmethylphenidate hydrochloride. The three stimulant layers of the trimodal, pulsatile release tablet may have the following composition:

| Stimulant layer | Ingredient | w/w % |
|---|---|---|
| First Stimulant layer | dexmethylphenidate hydrochloride | 2.5-5.0 w/w % |
| | Prosolv ® EASYtab SP (all-in-one excipient component)* | 94.5-97.0 w/w % |
| | calcium sulfate | ≤1.0 w/w % |
| Second Stimulant layer | dexmethylphenidate hydrochloride | 4.0-8.0 w/w % |
| | Prosolv ® EASYtab SP* | 83.0-87.0 w/w % |
| | calcium sulfate | ≤1.0 w/w % |
| | hypromellose (hydroxypropyl methylcellulose) | 4.0-10.0 w/w % |
| Third Stimulant layer | dexmethylphenidate hydrochloride | 2.5-5.0 w/w % |
| | Prosolv ® EASYtab SP* | 94.5-97.0 w/w % |
| | calcium sulfate | ≤1.0 w/w % |

*Also indicates cumulative w/w % of microcrystalline cellulose, colloidal silicon dioxide, sodium starch glycolate and sodium stearyl fumarate.

The first stimulant layer contains a first stimulant pulse that is about 35% of the total stimulant dose in the tablet. The second stimulant layer contains a second stimulant pulse that is about 45% of the total stimulant dose in the tablet. The third stimulant layer contains a third stimulant pulse that is about 20% of the total stimulant dose in the tablet.

The outer and inner erosion barrier layers have the following composition:

| Ingredient | Percentage (by weight) |
|---|---|
| Glyceryl behenate (Compritol 888) | 35%-45% |
| L-HPC LH-21 | 15%-25% |
| L-HPC LH-32 | 25%-35% |
| HPC Type L | 4%-8% |
| Colloidal silicon dioxide (Aerosil 200 Pharma) | ≤1% |

The trimodal, precision-timed pulsatile release tablet is structured generally as shown in FIG. 2. The three stimulant layers are incorporated at specific and controlled positions within the tablet. The first stimulant layer is positioned as a surface of the tablet and on an outer erosion barrier layer. The second stimulant layer is positioned between the outer erosion barrier layer and an inner erosion barrier layer. The third and final stimulant layer is positioned at the center of the tablet and surrounded by the inner erosion barrier layer. The tablet includes 240 mg of the outer erosion barrier layer and 125 mg of the inner erosion barrier layer.

Figure 5:
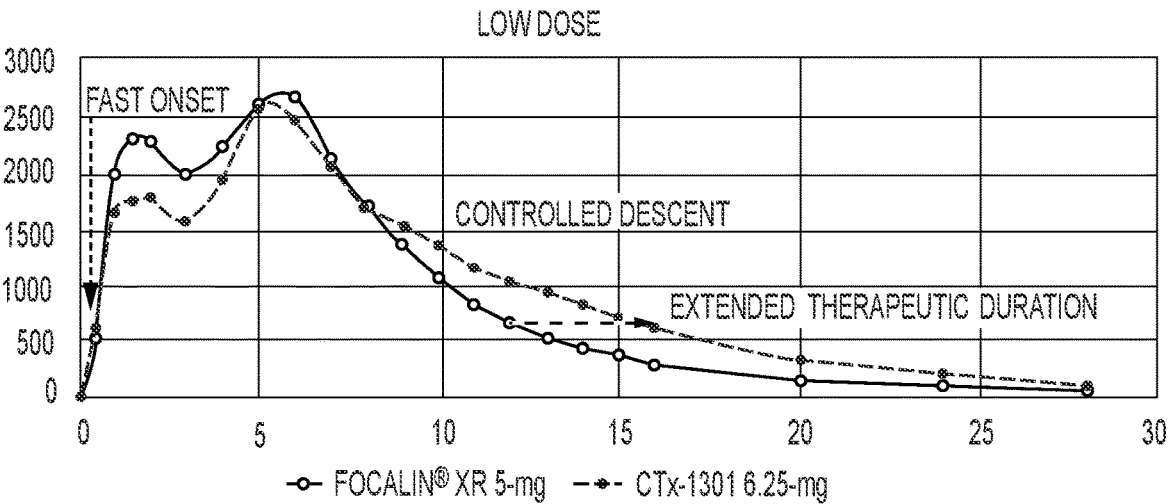
FIG. 5 shows dexmethylphenidate concentrations in plasma over time in a comparison of the trimodal, pulsatile release tablet disclosed herein to Focalin XR.

The trimodal, pulsatile release tablet described herein and a Focalin XR capsule containing 5 mg of dexmethylphenidate hydrochloride are orally administered to different patients. Plasma concentration of dexmethylphenidate hydrochloride is measured periodically after oral administration to patients. FIG. 5 shows the curves of stimulant concentration in plasma over time.

As shown in FIG. 5, the Focalin XR releases a first pulse of dexmethylphenidate soon after administration to a patient. The delayed, second release of Focalin XR begins around 3 hours administration to a patient and is complete by about 6 hours. Focalin XR has only two releases of dexmethylphenidate. The therapeutic effectiveness of Focalin XR containing 5 mg of dexmethylphenidate hydrochloride ends about 12 hours after administration to a patient.

As shown in FIG. 5, the trimodal, pulsatile release tablet (designated "CTx-1301") releases the first stimulant pulse of dexmethylphenidate soon after administration to a patient. This first release is substantially complete within 30 minutes. The delayed release of the second stimulant pulse begins around 3 hours after administration to a patient and is substantially complete around 5-5.25 hours. The second release is a sustained release for about 120-135 minutes. The third stimulant pulse is released around 9 hours after administration of the tablet to a patient. As a result of the third stimulant pulse, the trimodal, pulsatile release tablet disclosed herein has an extended bioavailability, compared to Focalin XR, until about 16 hours after administration of the pulsed-release capsule to the patient. The consistent bioavailability of dexmethylphenidate provided by the trimodal, pulsatile release tablet prevents or lessens the effects of a crash or rebound effect.

Example 2

A trimodal, precision-timed pulsatile release tablet having a total of 50 mg of dexmethylphenidate hydrochloride is compared to Focalin XR containing a total of 40 mg of dexmethylphenidate hydrochloride. A trimodal, pulsatile release tablet is manufactured and has the same structure as described in Example 1. The composition and amount outer and inner erosion barrier layers are the same as described in Example 1.

To account for the increased total amount of dexmethylphenidate hydrochloride, the three stimulant layers of the trimodal, pulsatile release tablet may have the following composition:

stimulant pulse that is about 45% of the total stimulant dose in the tablet. The third stimulant layer contains a third stimulant pulse that is about 20% of the total stimulant dose in the tablet.

Figure 6:
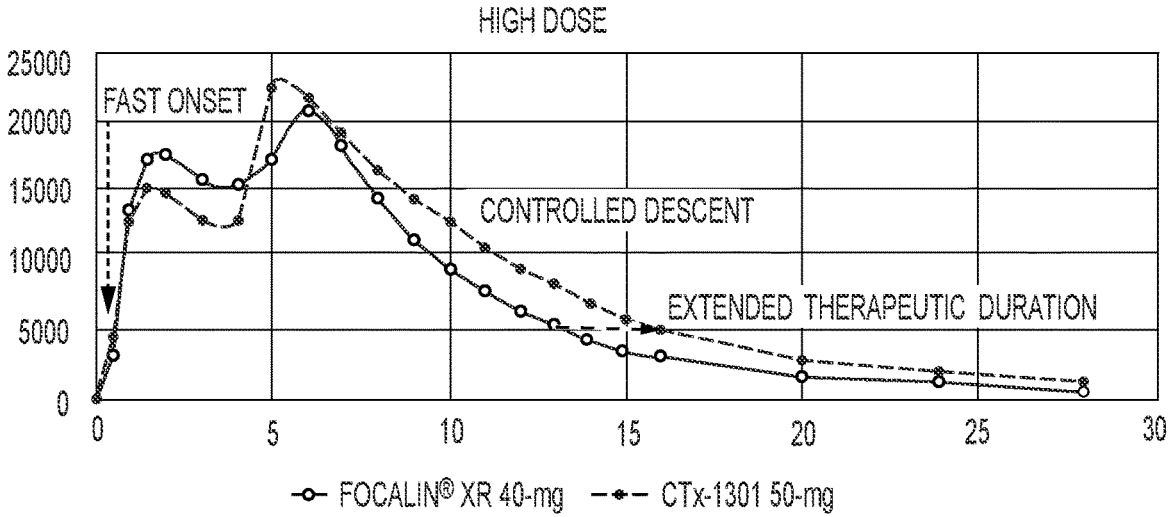
FIG. 6 shows dexmethylphenidate concentrations in plasma over time in another comparison of the trimodal, pulsatile release tablet disclosed herein to Focalin XR

The trimodal, precision-timed pulsatile release tablet described in this Example 2 and a Focalin XR capsule containing 40 mg of dexmethylphenidate hydrochloride are orally administered to different patients. Plasma concentration of dexmethylphenidate hydrochloride is measured periodically after oral administration to patients. FIG. 6 shows the curves of stimulant concentration in plasma over time with similar results as in Example 1

As shown in FIG. 6, the Focalin XR releases a first pulse of dexmethylphenidate soon after administration to a patient. The delayed, second release of Focalin XR begins around 3.5 hours administration to a patient and is complete by about 6 hours. Focalin XR is bimodal and has only two releases of dexmethylphenidate. The bioavailability of dexmethylphenidate with Focalin XR falls below therapeutic level about 12 hours after administration to a patient.

As shown in FIG. 6, the trimodal, pulsatile release tablet of this Example 2 (designated "CTx-1301") releases the first stimulant pulse of dexmethylphenidate soon after administration to a patient. This first release is substantially complete within 30 minutes. The delayed release of the second stimulant pulse begins around 3.5 hours after administration to a patient and is substantially complete around 5-5.25 hours. The second release is a sustained release for about 90-105 minutes. The third stimulant pulse is released around 9 hours after administration of the tablet to a patient. As in Example 1, the trimodal, pulsatile release tablet disclosed herein has an extended and sustained bioavailability, compared to Focalin XR, up to 16 hours after administration of the trimodal, pulsatile release tablet to the patient. The consistent bioavailability of dexmethylphenidate provided by the trimodal, pulsatile release tablet prevents or lessens the effects of a crash or rebound effect.

Example 3

The occurrence and types of TEAEs associated with the trimodal, precision-timed pulsatile release tablets described herein are compared to those associated with Focalin XR. Patients are treated with the trimodal, pulsatile release tablets described in Examples 1 and 2 (total stimulant dose of 6.25 mg and 50 mg, respectively) or Focalin XR having a total stimulant dose of 5 mg or 40 mg (also as described

| Stimulant layer | Ingredient | w/w % |
|---|---|---|
| First Stimulant layer | dexmethylphenidate hydrochloride | 17.5-23.0 w/w % |
| | Prosolv ® EASYtab SP (all-in-one excipient component)* | 76.0-82.0 w/w % |
| | calcium sulfate | ≤1.0 w/w % |
| Second Stimulant layer | dexmethylphenidate hydrochloride | 43.0-47.0 w/w % |
| | Prosolv ® EASYtab SP* | 44.0-48.0 w/w % |
| | calcium sulfate | ≤1.0 w/w % |
| | hypromellose (hydroxypropyl methylcellulose) | 4.0-10.0 w/w % |
| Third Stimulant layer | dexmethylphenidate hydrochloride | 17.5-23.0 w/w % |
| | Prosolv ® EASYtab SP* | 76.0-82.0 w/w % |
| | calcium sulfate | ≤1.0 w/w % |

*Also indicates cumulative w/w % of microcrystalline cellulose, colloidal silicon dioxide, sodium starch glycolate and sodium stearyl fumarate.

As in Example 1, the first stimulant layer contains a first stimulant pulse that is about 35% of the total stimulant dose in the tablet. The second stimulant layer contains a second in Examples 1 and 2). A summary of the single dose TEAEs is provided in Table 2 below. As shown in Table 2, the trimodal, pulsatile release tablets of Examples 1 and 2 provide a decrease in the number of patients who experience a TEAE (17 vs. 25), which represents an over 28% reduction compared to Focalin XR.

TABLE 2

| Category | Trimodal, pulsatile release tablet N = 42 n (%) | Focalin XR N = 44 n (%) |
|---|---|---|
| Patients with at least one TEAE | 17 (40.5%) | 25 (56.8%) |
| Subjects discontinued due to TEAE | 0 | 2 (4.5%) |
| TEAES by severity | | |
| Mild | 17 (40.5%) | 23 (52.3%) |
| Moderate | 0 | 2 (4.5%) |
| Severe | 0 | 0 |

The most common TEAEs for the pulsed-release tablets of Examples 1 and 2 are tachycardia, nausea, and headache. The most common TEAEs for Focalin XR are tachycardia, palpitations, headache and euphoric mood. Table 3 identifies occurrences of specific types of TEAEs by system organ class (SOC):

TABLE 3

| TEAE | Trimodal, pulsatile release tablet N = 42 n (%) | Focalin XR N = 44 n (%) |
|---|---|---|
| Cardiac Disorders | 3 (7.1%) | 7 (15.9%) |
| Eye Disorders | 1 (2.4%) | 0 |
| Gastrointestinal Disorders | 6 (14.3%) | 6 (13.6%) |
| General Disorders and Administration Site Conditions | 3 (7.1%) | 10 (22.7%) |
| Infections and Infestations | 0 | 1 (2.3%) |
| Injury, Poisoning, and Procedural Complications | 0 | 1 (2.3%) |
| Investigations | 0 | 1 (2.3%) |
| Metabolism and Nutrition Disorders | 2 (4.8%) | 1 (2.3%) |
| Musculoskeletal and Connective Tissue Disorders | 1 (2.4%) | 0 |
| Nervous System Disorders | 5 (11.9%) | 6 (13.6%) |
| Psychiatric Disorders | 8 (19.0%) | 4 (9.1%) |
| Skin and Subcutaneous Tissue Disorders | 0 | 1 (2.3%) |
| Vascular Disorders | 0 | 2 (4.5%) |

Table 4 shows the TEAEs related to the total stimulant doses of the trimodal, pulsatile release tablet tablets of Examples 1 and 2 and Focalin XR:

TABLE 4

| Category | Focalin XR 5 mg N = 41 n (%) | Example 1 Tablet 6.25 mg N = 39 n (%) | Focalin XR 40 mg N = 43 n (%) | Example 2 Tablet 50 mg N = 42 n (%) |
|---|---|---|---|---|
| Subjects with at least one TEAE | 7 (17.1%) | 4 (10.3%) | 22 (51.2%) | 14 (33.3%) |

While the present invention has been described in detail, the present invention is not limited to the foregoing embodiments described above. Modifications may be made without departing from the concept of the present invention.

The invention claimed is:

1. A trimodal, pulsatile release tablet for oral administration of a stimulant comprising:

(a) a first stimulant layer comprising (i) a first pulse of about 30% to about 40% of the total stimulant in the tablet, wherein the first pulse is released within about 10 to about 45 minutes after oral administration of the tablet to a patient, (ii) calcium sulfate, (iii) microcrystalline cellulose, (iv) colloidal silicon dioxide, (v) sodium starch glycolate, and (vi) sodium stearyl fumarate;

(b) a second stimulant layer comprising (i) a second pulse of about 40% to about 50% of the total stimulant in the tablet, wherein release of the second pulse begins about 3 to about 5 hours following oral administration of the tablet to a patient, and release of the second pulse is sustained for about −30 to about 135 minutes, (ii) calcium sulfate, (iii) hypromellose, (iv) microcrystalline cellulose, (v) colloidal silicon dioxide, (vi) sodium starch glycolate and (vii) sodium stearyl fumarate; and (c) a third stimulant layer comprising (i) a third pulse of about 15% to about 25% of the total stimulant in the tablet, wherein the third pulse is delayed in release until about 5 hours to about 10 hours following oral administration of the tablet to a patient, (ii) calcium sulfate, (iii) microcrystalline cellulose, (iv) colloidal silicon dioxide, (v) sodium starch glycolate, and (vi) sodium stearyl fumarate;

wherein the tablet is structured such that the first stimulant layer is positioned as a surface of the tablet and on an outer erosion barrier layer, the second stimulant layer is positioned between the outer erosion barrier layer and an inner erosion barrier layer such that it is surrounded by the outer and inner erosion barrier layers, and the third stimulant layer is positioned at the center of the tablet and surrounded by the inner erosion barrier layer;

wherein the first stimulant layer comprises 2.5 w/w % to about 25 w/w % of stimulant, about 1 w/w % or less of calcium sulfate and about 75 w/w % to about 98 w/w % cumulatively of microcrystalline cellulose, colloidal silicon dioxide, sodium starch glycolate and sodium stearyl fumarate; the second stimulant layer comprises about 5 w/w % to about 50 w/w % of stimulant, about 1 w/w % or less of calcium sulfate, about 4 w/w % to about 10 w/w % of hypromellose, and about 40 w/w % to about 90 w/w % cumulatively of microcrystalline cellulose, colloidal silicon dioxide, sodium starch glycolate and sodium stearyl fumarate; the third stimulant layer comprises 2.5 w/w % to about 25 w/w % of stimulant, about 1 w/w % or less of calcium sulfate, and about 75 w/w % to about 98 w/w % cumulatively of microcrystalline cellulose, colloidal silicon dioxide, sodium starch glycolate and sodium stearyl fumarate;

wherein the outer and inner erosion barrier layers each comprise about 35% to about 45% by weight of glyceryl behenate, about 15% to about 25% by weight of LH-21, about 25% to about 35% by weight of LH-32 and about 4% to about 8% by weight of hydroxypropyl cellulose;

wherein the thickness of the outer erosion barrier layer is about 574 to 888 microns and the thickness of the inner erosion barrier layer is about 862 to 1071 microns; and wherein the stimulant is methylphenidate or a pharmaceutically acceptable salt thereof.

2. The tablet of claim 1, wherein release of the third pulse begins about 6 to about 9 hours following oral administration of the tablet to a patient.

3. The tablet of claim 1, wherein the first pulse releases about 35% of the total stimulant in the tablet.

4. The tablet of claim 1, wherein the second pulse releases about 45% of the total stimulant in the tablet.

5. The tablet of claim 1, wherein the third pulse releases about 20% of the total stimulant in the tablet.

6. The tablet of claim 1, wherein release of the second pulse begins about 3 to about 4 hours following oral administration of the tablet to a patient.

7. The tablet of claim 1, wherein release of the third pulse begins about 7 to about 8 hours following oral administration of the tablet to a patient.

8. The tablet of claim 1, wherein the second pulse is sustained for about 90 minutes.

9. The tablet of claim 1, wherein the outer and inner erosion barrier layers each comprise about 37.5% to about 42.5% by weight of glyceryl behenate, about 20% to about 23% by weight of LH-21, about 27.5% to about 32.5% by weight of LH-32, and about 5% to about 7% by weight of hydroxypropyl cellulose.

10. The tablet of claim 1, wherein the hydroxypropyl cellulose is hydroxypropyl cellulose Type L.

11. The tablet of claim 1, wherein the outer and inner erosion barrier layers each comprise about 1% or less by weight of colloidal silicon dioxide.

12. The tablet of claim 1, wherein the first stimulant layer is about 600 microns thick, the second stimulant layer is about 750 microns thick and the third stimulant layer is about 2.03 mm thick with a flat-faced radius edge.

13. The tablet of claim 1, wherein the second stimulant layer is positioned between the first stimulant layer and the third stimulant layer.

14. The tablet of claim 1, wherein the third stimulant layer is positioned between the first stimulant layer and the second stimulant layer.

15. The tablet of claim 1, wherein:

the total stimulant dose of the tablet is 50 mg;

the first stimulant layer comprises 17.5 to 23.0 w/w % of stimulant, 1 w/w % or less of calcium sulfate and 76.0 to 82.0 w/w % cumulatively of microcrystalline cellulose, colloidal silicon dioxide, sodium starch glycolate, and sodium stearyl fumarate;

the second stimulant layer comprises 43.0 to 47.0 w/w % of stimulant, 1 w/w % or less of calcium sulfate, 4.0 to 10.0 w/w % of hypromellose and 44.0 to 48.0 w/w % cumulatively of microcrystalline cellulose, colloidal silicon dioxide, sodium starch glycolate, and sodium stearyl fumarate; and the third stimulant layer comprises 17.5 to 23.0 w/w % of stimulant, 1 w/w % or less of calcium sulfate and 76.0 to 82.0 w/w % cumulatively of microcrystalline cellulose, colloidal silicon dioxide, sodium starch glycolate, and sodium stearyl fumarate.

16. A method for extending the therapeutic duration of a stimulant, the method comprising administering the tablet of claim 1 to a patient in need thereof, wherein the therapeutic duration of the stimulant is effective for at least 14 hours after oral administration of the tablet to a patient.

17. A method of treatment of a disorder, condition, or disease for which a stimulant is generally indicated, the method comprising administering the tablet of claim 1 to a patient in need thereof.

18. The method of claim 1, wherein the disorder, condition, or disease is ADHD.

19. The tablet of claim 1, wherein the third stimulant layer is 1.97-2.03 mm thick.

\* \* \* \* \*